(12) United States Patent
Holzer et al.

(10) Patent No.: US 9,132,261 B2
(45) Date of Patent: *Sep. 15, 2015

(54) IN VIVO FILTER ASSEMBLY

(75) Inventors: Asher Holzer, Haifa (IL); Eli Bar, Moshav Megadim (IL); Ofir Paz, Rishon Lezion (IL)

(73) Assignee: INSPIREMD, LTD., Tel Aviv (IL)

( * ) Notice: Subject to any disclaimer, the term of this patent is extended or adjusted under 35 U.S.C. 154(b) by 1009 days.

This patent is subject to a terminal disclaimer.

(21) Appl. No.: 13/237,977

(22) Filed: Sep. 21, 2011

(65) Prior Publication Data

US 2012/0010649 A1 Jan. 12, 2012

Related U.S. Application Data

(62) Division of application No. 11/582,354, filed on Oct. 18, 2006, now Pat. No. 8,043,323.

(51) Int. Cl.
*A61F 2/06* (2013.01)
*A61M 25/10* (2013.01)
*A61F 2/01* (2006.01)

(52) U.S. Cl.
CPC .............. *A61M 25/104* (2013.01); *A61F 2/013* (2013.01); *A61F 2002/018* (2013.01); *A61F 2230/0006* (2013.01); *A61F 2230/008* (2013.01); *A61M 2025/1059* (2013.01); *A61M 2025/1081* (2013.01)

(58) Field of Classification Search
USPC ........................... 606/200, 191, 194, 195, 198
See application file for complete search history.

(56) References Cited

U.S. PATENT DOCUMENTS

| 4,164,045 A | 8/1979 | Bokros et al. |
|---|---|---|
| 4,300,244 A | 11/1981 | Bokros |
| 4,321,711 A | 3/1982 | Mano |
| 4,425,908 A | 1/1984 | Simon |
| 4,723,549 A | 2/1988 | Wholey et al. |
| 4,832,688 A | 5/1989 | Sagae et al. |
| 4,865,017 A | 9/1989 | Shinozuka |
| 4,873,978 A | 10/1989 | Ginsburg |
| 4,969,891 A | 11/1990 | Gewertz |

(Continued)

FOREIGN PATENT DOCUMENTS

| CN | 1414840 A | 4/2003 |
|---|---|---|
| EP | 0839506 A1 | 5/1998 |

(Continued)

OTHER PUBLICATIONS

European Patent Application # 07827415.6 Search report dated Feb. 13, 2013.

(Continued)

*Primary Examiner* — Vy Bui
(74) *Attorney, Agent, or Firm* — Haynes and Boone, LLP

(57) ABSTRACT

Disclosed is an assembly for filtering debris flowing in an in vivo fluid stream, the assembly comprising at least one balloon configured to volumetrically expand and, during at least a portion of the expansion, operatively connect with a filter, and to contract following the expansion. The assembly further comprising a filter configured to operatively connect with the at least one balloon during at least a portion of the volumetric expansion of the at least one balloon, such that the filter expands during the operative connection in order to filter debris from a fluid flowing in a fluid stream within which the expanded filter is disposed.

20 Claims, 9 Drawing Sheets

(56) References Cited

U.S. PATENT DOCUMENTS

| | | |
|---|---|---|
| 4,990,156 A | 2/1991 | Lefebvre |
| 4,998,539 A | 3/1991 | Delsanti |
| 5,019,090 A | 5/1991 | Pinchuk |
| 5,122,154 A | 6/1992 | Rhodes |
| 5,152,777 A | 10/1992 | Goldberg et al. |
| 5,171,233 A | 12/1992 | Amplatz et al. |
| 5,192,286 A | 3/1993 | Phan et al. |
| 5,236,447 A | 8/1993 | Kubo et al. |
| 5,330,482 A | 7/1994 | Gibbs et al. |
| 5,366,504 A | 11/1994 | Andersen et al. |
| 5,382,261 A | 1/1995 | Palmaz |
| 5,383,887 A | 1/1995 | Nadal |
| 5,403,341 A | 4/1995 | Solar |
| 5,421,955 A | 6/1995 | Lau et al. |
| 5,470,313 A | 11/1995 | Crocker et al. |
| 5,486,183 A | 1/1996 | Middleman et al. |
| 5,569,295 A | 10/1996 | Lam |
| 5,591,228 A | 1/1997 | Edoga |
| 5,713,948 A | 2/1998 | Uflacker |
| 5,769,884 A | 6/1998 | Solovay |
| 5,824,037 A | 10/1998 | Fogarty et al. |
| 5,827,324 A | 10/1998 | Cassell et al. |
| 5,833,651 A | 11/1998 | Donovan et al. |
| 5,843,116 A | 12/1998 | Crocker et al. |
| 5,843,161 A | 12/1998 | Solovay |
| 5,871,538 A | 2/1999 | Dereume |
| 5,908,448 A | 6/1999 | Roberts et al. |
| 5,919,225 A | 7/1999 | Lau et al. |
| 5,941,896 A | 8/1999 | Kerr |
| 5,984,955 A | 11/1999 | Wisselink |
| 6,007,543 A | 12/1999 | Ellis et al. |
| 6,015,430 A | 1/2000 | Wall |
| 6,015,432 A | 1/2000 | Rakos et al. |
| 6,027,517 A | 2/2000 | Crocker et al. |
| 6,030,414 A | 2/2000 | Taheri |
| 6,042,597 A | 3/2000 | Kveen et al. |
| 6,066,167 A | 5/2000 | Lau et al. |
| 6,077,273 A | 6/2000 | Euteneuer et al. |
| 6,096,027 A | 8/2000 | Layne |
| 6,152,144 A | 11/2000 | Lesh et al. |
| 6,176,875 B1 | 1/2001 | Lenker et al. |
| 6,245,089 B1 * | 6/2001 | Daniel et al. ................. 606/200 |
| 6,254,627 B1 | 7/2001 | Freidberg |
| 6,263,880 B1 | 7/2001 | Parker et al. |
| 6,306,162 B1 | 10/2001 | Patel |
| 6,340,364 B2 | 1/2002 | Kanesaka |
| 6,348,065 B1 | 2/2002 | Brown et al. |
| 6,357,104 B1 | 3/2002 | Myers |
| 6,361,558 B1 | 3/2002 | Hieshima et al. |
| 6,369,039 B1 | 4/2002 | Palasis et al. |
| 6,371,962 B1 | 4/2002 | Ellis et al. |
| 6,383,171 B1 | 5/2002 | Gifford et al. |
| 6,432,129 B2 | 8/2002 | DiCaprio |
| 6,436,132 B1 | 8/2002 | Patel et al. |
| 6,447,796 B1 | 9/2002 | Vook et al. |
| 6,451,051 B2 | 9/2002 | Drasler et al. |
| 6,461,381 B2 | 10/2002 | Israel et al. |
| 6,464,722 B2 | 10/2002 | Israel et al. |
| 6,468,230 B2 | 10/2002 | Muni et al. |
| 6,488,703 B1 | 12/2002 | Kveen et al. |
| 6,506,203 B1 | 1/2003 | Boyle et al. |
| 6,540,773 B2 | 4/2003 | Dong |
| 6,554,855 B1 | 4/2003 | Dong |
| 6,602,285 B1 | 8/2003 | Von Oepen et al. |
| 6,641,607 B1 | 11/2003 | Hossainy et al. |
| 6,645,239 B1 | 11/2003 | Park et al. |
| 6,669,717 B2 | 12/2003 | Marotta et al. |
| 6,669,961 B2 | 12/2003 | Kim et al. |
| 6,673,814 B2 | 1/2004 | Joshi et al. |
| 6,676,695 B2 | 1/2004 | Solem |
| 6,682,554 B2 | 1/2004 | Oepen et al. |
| 6,702,849 B1 | 3/2004 | Dutta et al. |
| 6,712,834 B2 | 3/2004 | Yassour et al. |
| 6,712,842 B1 | 3/2004 | Gifford, III et al. |
| 6,755,856 B2 | 6/2004 | Fierens et al. |
| 6,802,851 B2 | 10/2004 | Jones et al. |
| 6,808,533 B1 | 10/2004 | Goodwin et al. |
| 6,818,014 B2 | 11/2004 | Brown et al. |
| 6,827,731 B2 | 12/2004 | Armstrong et al. |
| 6,835,189 B2 | 12/2004 | Musbach et al. |
| 6,893,457 B2 | 5/2005 | Dong |
| 6,902,522 B1 | 6/2005 | Walsh et al. |
| 6,918,920 B1 | 7/2005 | Wang et al. |
| 6,919,100 B2 | 7/2005 | Narayanan |
| 6,929,658 B1 | 8/2005 | Freidberg et al. |
| 6,932,832 B2 | 8/2005 | Patel et al. |
| 6,939,374 B2 | 9/2005 | Banik et al. |
| 6,939,376 B2 | 9/2005 | Shulze et al. |
| 6,953,476 B1 | 10/2005 | Shalev |
| 6,981,986 B1 | 1/2006 | Brown et al. |
| 6,997,946 B2 | 2/2006 | Girton et al. |
| 7,011,676 B2 | 3/2006 | Dong |
| 7,037,330 B1 | 5/2006 | Rivelli, Jr. et al. |
| 7,041,129 B2 | 5/2006 | Rourke et al. |
| 7,083,644 B1 | 8/2006 | Moroni |
| 7,198,638 B2 | 4/2007 | Dong |
| 7,491,225 B2 | 2/2009 | Weber et al. |
| 7,594,926 B2 * | 9/2009 | Linder et al. .................. 623/1.11 |
| 7,621,870 B2 * | 11/2009 | Berrada et al. ................. 600/200 |
| 7,722,634 B2 | 5/2010 | Panetta et al. |
| 7,996,993 B2 | 8/2011 | Gray et al. |
| 8,097,015 B2 | 1/2012 | Devellian |
| 2002/0022860 A1 | 2/2002 | Borillo et al. |
| 2002/0045917 A1 | 4/2002 | Ambrisco et al. |
| 2002/0082685 A1 | 6/2002 | Sirhan et al. |
| 2002/0111668 A1 | 8/2002 | Smith |
| 2002/0128679 A1 | 9/2002 | Turovskiy et al. |
| 2002/0161393 A1 | 10/2002 | Demond et al. |
| 2003/0028239 A1 | 2/2003 | Dong |
| 2003/0055452 A1 | 3/2003 | Joergensen et al. |
| 2003/0093112 A1 | 5/2003 | Addis |
| 2003/0100945 A1 | 5/2003 | Yodfat et al. |
| 2003/0130718 A1 | 7/2003 | Palmas et al. |
| 2003/0149464 A1 | 8/2003 | Dong |
| 2003/0176884 A1 | 9/2003 | Berrada et al. |
| 2003/0229389 A1 | 12/2003 | Escano |
| 2004/0030377 A1 | 2/2004 | Dubson et al. |
| 2004/0054402 A1 | 3/2004 | DiCarlo |
| 2004/0068314 A1 | 4/2004 | Jones et al. |
| 2004/0111142 A1 | 6/2004 | Rourke et al. |
| 2004/0116960 A1 | 6/2004 | Demond et al. |
| 2004/0143272 A1 | 7/2004 | Cully et al. |
| 2004/0158312 A1 | 8/2004 | Chouinard et al. |
| 2004/0225322 A1 | 11/2004 | Garrison et al. |
| 2004/0236407 A1 | 11/2004 | Fierens et al. |
| 2004/0267347 A1 | 12/2004 | Cervantes |
| 2004/0267352 A1 | 12/2004 | Davidson |
| 2005/0038503 A1 | 2/2005 | Greenhalgh et al. |
| 2005/0049680 A1 | 3/2005 | Fischell et al. |
| 2005/0110214 A1 | 5/2005 | Shank et al. |
| 2005/0119688 A1 | 6/2005 | Bergheim |
| 2005/0171591 A1 | 8/2005 | McHale et al. |
| 2005/0182473 A1 | 8/2005 | Eidenschink et al. |
| 2005/0187140 A1 | 8/2005 | Hunter et al. |
| 2005/0222607 A1 | 10/2005 | Palmer et al. |
| 2005/0277976 A1 | 12/2005 | Galdonik et al. |
| 2006/0009835 A1 | 1/2006 | Osborne et al. |
| 2006/0085064 A1 | 4/2006 | Tuch |
| 2006/0116748 A1 | 6/2006 | Kaplan et al. |
| 2006/0155359 A1 | 7/2006 | Watson |
| 2006/0175727 A1 | 8/2006 | Fierens et al. |
| 2006/0259131 A1 | 11/2006 | Molaei et al. |
| 2006/0259137 A1 | 11/2006 | Artof et al. |
| 2007/0043428 A1 | 2/2007 | Jennings et al. |
| 2007/0135890 A1 | 6/2007 | Dong |
| 2007/0179593 A1 | 8/2007 | Fierens et al. |
| 2007/0179601 A1 | 8/2007 | Fierens et al. |
| 2007/0208374 A1 | 9/2007 | Boyle et al. |
| 2007/0213800 A1 | 9/2007 | Fierens et al. |
| 2007/0270902 A1 | 11/2007 | Slazas et al. |
| 2007/0276468 A1 | 11/2007 | Holzer et al. |
| 2008/0023346 A1 | 1/2008 | Vonderwalde |
| 2008/0172082 A1 | 7/2008 | Holzer et al. |
| 2009/0012598 A1 | 1/2009 | Abbate et al. |

(56) References Cited

U.S. PATENT DOCUMENTS

| | | |
|---|---|---|
| 2009/0138070 A1 | 5/2009 | Holzer et al. |
| 2009/0248133 A1 | 10/2009 | Bloom et al. |
| 2010/0056907 A1 | 3/2010 | Rappaport et al. |
| 2010/0204772 A1 | 8/2010 | Holzer et al. |
| 2010/0222805 A1 | 9/2010 | Pal et al. |
| 2010/0241214 A1 | 9/2010 | Holzer et al. |
| 2010/0324664 A1 | 12/2010 | Holzer et al. |
| 2011/0098739 A1 | 4/2011 | Bates |

FOREIGN PATENT DOCUMENTS

| | | |
|---|---|---|
| WO | 8809683 A1 | 12/1988 |
| WO | 9929262 A1 | 6/1999 |
| WO | 0130266 A1 | 5/2001 |
| WO | 03018079 A1 | 3/2003 |
| WO | 03022325 A2 | 3/2003 |
| WO | 2006010130 A1 | 1/2006 |
| WO | 2006116636 A1 | 11/2006 |
| WO | 2006126182 A2 | 11/2006 |
| WO | 2007067451 A2 | 6/2007 |
| WO | 2008047367 A2 | 4/2008 |
| WO | 2008047368 A2 | 4/2008 |
| WO | 2008047369 A2 | 4/2008 |
| WO | 2008062414 A2 | 5/2008 |

OTHER PUBLICATIONS

European Patent Application # 07827227.5 Search report dated Feb. 25, 2013.
U.S. Appl. No. 11/920,972 Office action dated Apr. 16, 2013.
European Patent Application # 07827228.3 Search report dated Mar. 8, 2013.
Israeli Patent Application # 198665 Office action dated Apr. 25, 2013.
U.S. Appl. No. 11/920,972 Official Action dated Nov. 30, 2011.
U.S. Appl. No. 11/920,972 Advisory Action dated Feb. 10, 2012.
U.S. Appl. No. 12/445,980 Official Action dated Dec. 5, 2011.
U.S. Appl. No. 12/791,008 Office action dated Oct. 4, 2012.
U.S. Appl. No. 11/920,972 Office action dated Oct. 9, 2012.
IL Patent Application # 198,190 Office action dated Nov. 22, 2012.
Haj et al., "Acquired Haemophilia A May be Associated with Clopidogrel", British Medical Journal, vol. 329, p. 323, Aug. 7, 2004.
Zakarija et al., "Clopidogrel-Associated TTP: An Update of Pharmacovigilance Efforts Conducted by Independent Researchers, Pharmaceutical Suppliers, and the Food and Drug Administration", STROKE—Journal of American Heart Association, vol. 35, pp. 533-537, Jan. 5, 2004.
Liistro et al., "Late Acute Thrombosis After Paclitaxel Eluting Stent Implantation", HEART Medical Journal, vol. 86, pp. 262-264, Sep. 2001.
Nguyen et al.,"Resistance to Clopidogrel: A Review of the Evidence", Journal of the American College of Cardiology, vol. 45, No. 8, pp. 1157-1164, Apr. 19, 2005.
Fayad et al., "Clinical Imaging of the High-Risk or Vulnerable Atherosclerotic Plaque", American Heart Association, Circulation Research, vol. 89, pp. 305-316, Aug. 17, 2001.
Chinese Patent Application # 200780046697.4 Official Action dated Apr. 6, 2011.
International Patent Application PCT/IL07/01442 Search Report dated Aug. 27, 2008.
International Patent Application PCT/IL07/01253 Search report dated Jun. 13, 2008.
International Patent Application PCT/IL07/01254 Search Report dated Sep. 30, 2008.
International Patent Application PCT/IL07/01255 Search Report dated Sep. 25, 2008.
U.S. Appl. No. 11/582,354 Official Action dated Jun. 14, 2010.
U.S. Appl. No. 11/797,168 Official Action dated Feb. 23, 2009.
U.S. Appl. No. 11/797,168 Official Action dated Nov. 17, 2009.
Chinese Patent Application # 200780046676.2 Office Action dated Apr. 28, 2011.
U.S. Appl. No. 12/445,972 Office Action dated Aug. 22, 2011.
Chinese Patent Application # 200780046659.9 Office Action dated May 11, 2011.
Chinese Patent Application # 200780046659.9 Office Action dated Oct. 26, 2011.
U.S. Appl. No. 11/582,354 Official Action dated Nov. 4, 2010.
U.S. Appl. No. 12/445,968 Official Action dated Jan. 25, 2011.
U.S. Appl. No. 11/920,972 Official Action dated Mar. 31, 2011.
Israel Patent Application # 198189 Official Action dated Jun. 1, 2011.
Israel Patent Application # 187516 Official Action dated Apr. 14, 2011.
Israel Patent Application # 198190 Official Action dated Jun. 1, 2011.
Israel Patent Application # 198665 Official Action dated Jun. 1, 2011.
U.S. Appl. No. 12/445,980 Official Action dated Apr. 28, 2011.
U.S. Appl. No. 12/445,968 Official Action dated Jun. 17, 2011.
International Application PCT/IB2011/055758 Search Report dated May 14, 2012.
U.S. Appl. No. 12/791,008 Official Action dated Mar. 26, 2012.
U.S. Appl. No. 12/445,972 Official Action dated Jun. 18, 2012.
U.S. Appl. No. 12/445,972 Official Action dated Mar. 26, 2012.
Israel Patent Application # 198188 Official Action dated Apr. 16, 2012.
Chinese Patent Application # 200780043259.2 Official Action dated Mar. 31, 2012.
Chinese Patent Application # 200780046697.4 Official Action dated Mar. 23, 2012.

* cited by examiner

IN VIVO FILTER ASSEMBLY

CROSS-REFERENCE TO RELATED APPLICATION

This applicaton is a division of U.S. patent application Ser. No. 11/582,354, filed Oct. 18, 2006.

FIELD OF THE INVENTION

The present invention relates generally to in vivo filters that filter debris from a fluid stream in which the filter is disposed.

BACKGROUND OF THE INVENTION

In 1977 Andreas Gruntzig performed the first successful balloon angioplasty on an obstructed human artery, thereby opening the vessel and allowing improved flow of blood.

Balloon angioplasty is a catheter-based procedure in which a long, thin tube with a deflated balloon at the tip is inserted into an artery. The balloon is guided to a stenotic lesion using X-ray fluoroscopy, rapidly inflated to a pressure of several atmospheres and deflated. Several rounds of inflation and deflation cause the stenotic lesion to crack and squash radially outward, thereby opening the obstructed lumen.

Balloon Angioplasty may be indicated for improving circulation to virtually any stenosed organ vasculature or peripheral vasculature, including opening occluded vessels during an acute heart attack; and in place of surgical endarterectomy, treatment of carotid artery stenosis, in high-risk surgical patients.

A problem associated with balloon angioplasty is that the stenotic lesion may release debris that travels to vital organs, for example the brain and/or lungs, causing vascular blockage, tissue necrosis and/or patient death.

To prevent such draconian sequela, a number of in vivo debris filter devices have been developed that are designed to capture debris released from stenotic lesions during an angioplasty procedure.

Using a guide passage, such a debris filter is positioned downstream of the intended angioplasty site and expanded to press against the tissue surrounding the lumen, thereby effectively filtering all blood passing through the lumen. A balloon angioplasty catheter is then introduced into the artery and the balloon is positioned adjacent the stenotic lesion. The balloon is inflated, the lesion releases debris and the filter captures the debris. After deflation and removal of the balloon, the filter is contracted and removed with the captured debris.

The use of in vivo debris filters during balloon angioplasty, however, may fail to prevent vascular blockage, tissue necrosis and/or patient death. To be effective, in vivo debris filters are positioned quite a distance downstream from the lesion undergoing angioplasty; considerably raising the chances that a vessel branching off the treated vessel will be located between the angioplasty balloon and the filter. Debris generated by the angioplasty will likely find its way into the branch vessel and travel to the lungs or brain, causing the above-noted sequela.

Additionally the filter itself may pose a health hazard to the patient. The deployment zone for the filter often comprises healthy vascular tissue. Positional adjustments and expansion of the filter against the healthy vascular tissue can cause tissue scars and plaques that, of themselves, provide a breeding ground for additional, full-blown, stenotic lesions.

In spite of the above-noted risk and health hazard, use of a debris filter is indicated for patients having "rupture-prone" lesions; stenotic lesions characterized by thin fibrous caps and large lipid cores. Even though it is impossible to introduce a filter once the balloon angioplasty has begun, in theory, pre-operative identification of a rupture-prone stenotic lesion would allow the patient and surgeon to weigh the risks and benefits of using an in vivo debris filter in addition to the angioplasty balloon catheter.

Unfortunately, the above theoretical solution is almost totally unworkable in practice because the very lesions that are rupture-prone are often not visible by x-ray angiography.

(Z. A. Fayad et al: "Clinical Imaging of the High-Risk or Vulnerable Atherosclerotic Plaque"; *Circulation Research.* 2001; 89: 305.)

The surgeon and patient, therefore, are left to grope in the dark for answers as to whether to risk patient health and deploy a debris filter.

In general, existing devices and technology present a number of additional disadvantages associated with the stand-alone in vivo debris filter, including:
1) the additional thousands of dollars to pay for each disposable filter for each surgery;
2) the difficulty in surgically deploying the filter in addition to a balloon angioplasty; and
3) the additional surgical fee charged by the surgeon for performing a second surgical procedure associated with the filter.

SUMMARY OF THE INVENTION

Some embodiments of the present invention successfully address at least some of the shortcomings of the prior art by providing an assembly for filtering debris flowing in an in vivo fluid stream, the assembly comprises a balloon configured to volumetrically expand and, during at least a portion of the expansion, operatively connect with a filter, thereby expanding the filter.

There is thus provided an assembly for filtering debris flowing in an in vivo fluid stream, the assembly comprising at least one balloon configured to volumetrically expand and, during at least a portion of the expansion, operatively connect with a filter, and to contract following the expansion. The assembly further comprising a filter configured to operatively connect with the at least one balloon during at least a portion of the volumetric expansion of the at least one balloon, such that the filter expands during the operative connection in order to filter debris from a fluid flowing in a fluid stream within which the expanded filter is disposed.

In embodiments, the at least one balloon comprises at least one proximal portion and at least one distal portion. In embodiments, and the operative connection between the at least one balloon and the filter occurs in the at least one proximal portion. In embodiments, the operative connection between the at least one balloon and the filter occurs in the at least one distal portion.

In embodiments, a maximal expansion diameter of the at least one distal portion is greater than a maximal expansion diameter of the at least one proximal portion. In embodiments, a maximal expansion diameter of the at least one proximal portion is greater than a maximal expansion diameter of the at least one distal portion.

In embodiments, the at least one balloon comprises at least one angioplasty balloon. In embodiments, the at least one balloon comprises at least two balloons, at least one first balloon and at least one second balloon.

In embodiments, the at least one first balloon is positioned proximally to the at least one second balloon. In embodiments, the at least one first balloon has a first maximal inflation diameter and the at least one second balloon has a second maximal inflation diameter.

In embodiments, at least a portion of the filter is configured to removably connect to a luminal aspect associated with the fluid stream, in response to pressure by the at least one balloon of between at least about one atmosphere and no more than about 20 atmospheres.

In embodiments, at least a portion of the filter is configured to remain removably connected to the luminal aspect during the contraction of the at least one balloon. In embodiments, the at least one balloon is configured to sequentially pass through at least two sequences of the expansion and contraction of the at least one balloon.

In embodiments, at least a portion of the filter is configured to remain removably connected to a luminal aspect associated with the fluid stream during at least a portion of the at least two sequences.

In embodiments, the assembly includes at least one cord operatively associated with the filter and configured to disconnect at least a portion of the filter from the luminal aspect when tension is applied to the at least one cord.

In embodiments, at least a portion of the filter is configured to disconnect from the luminal aspect in response to tension applied to the at least one cord of at least about one Newton.

In embodiments, at least a portion of the filter is configured to disconnect from the luminal aspect in response to tension applied to the at least one cord of no more than about 20 Newtons.

In embodiments, at least a portion of the filter includes a pressure-sensitive adhesive having an affinity for a tissue associated with an in vivo luminal aspect.

In embodiments, the adhesive is an adhesive from the group of adhesives comprising fibrin, biological glue, collagen, hydrogel, hydrocolloid, collagen alginate, and methylcellulose.

In embodiments, at least a portion of the filter is configured to removably connect to a luminal aspect associated with the fluid stream, in response to pressure by the at least one balloon of between at least about one atmosphere and no more than about 20 atmospheres.

In embodiments, at least a portion of the filter is configured to remain removably connected to the luminal aspect during the contraction of the at least one balloon.

In embodiments, the at least one balloon is configured to sequentially pass through at least two sequences of the expansion and contraction of the at least one balloon.

In embodiments, at least a portion of the filter is configured to remain removably connected to the luminal aspect during at least a portion the at least two sequences.

In embodiments, the assembly includes at least one cord operatively associated with the filter and configured to disconnect at least a portion of the filter from the luminal aspect when tension is applied to the at least one cord.

In embodiments, at least a portion of the filter is configured to disconnect from the luminal aspect in response to tension applied to the at least one cord of at least about one Newton.

In embodiments, at least a portion of the filter is configured to disconnect from the luminal aspect in response to tension applied to the at least one cord of no more than about 20 Newtons.

In embodiments, the assembly includes a compression sleeve comprising a substantially curved wall having a proximal end, a distal end and a lumen extending from the proximal end to the distal end, the lumen having a cross sectional diameter that is substantially smaller than the maximal cross sectional diameter of the luminal aspect and at least one cord operatively associated with the filter, at least a portion of the at least one cord slidingly juxtaposed within the compression sleeve lumen, such that in response to at least one first distal sliding of the sleeve while the at least one cord is held stationary, the filter is caused to disconnect from the luminal aspect.

In embodiments, in response to at least one second distal sliding of the sleeve while the at least one cord is held stationary, the filter is caused to radially contract such that a maximal cross sectional diameter of the filter is smaller that a cross sectional diameter of the sleeve lumen.

In embodiments, in response to at least one third distal sliding of the sleeve while the at least one cord is held stationary; at least a portion of the filter is caused to enter the sleeve lumen.

In embodiments, the at least one balloon comprises an outer wall having a distal end and a proximal end and an inner wall defining a lumen, the lumen extending from the distal end to the proximal end, and In embodiments, at least a portion of the at least one cord is configured to slidingly pass through the lumen.

In embodiments, the at least one cord is configured to pull at least a portion of the filter into contact with the distal end of the at least one balloon.

In embodiments, the assembly includes a catheter having a distal end and a proximal end and a lumen extending from the distal end to the proximal end, wherein the at least one balloon proximal end is operatively associated with the distal end of the catheter.

In embodiments, the at least one balloon lumen is substantially continuous with the catheter lumen.

In embodiments, at least a portion of the at least one cord additionally extends through the catheter lumen.

In embodiments, the filter includes a distal portion, a proximal portion, an opening to the filter associated with the proximal portion and at least one strut operatively associated with the proximal portion.

In embodiments, the assembly includes at least one cord operatively associated with the at least one strut, such that at least a portion of the opening is configured to contract radially inwardly in response to tension applied to the at least one cord.

In embodiments, the at least one strut comprises at least two struts operatively associated with the at least one cord.

In embodiments, each of the at least two struts is configured to resiliently flex outward to form at least one expanded cross sectional diameter.

In embodiments, the at least one expanded cross sectional diameter defines at least two sections, a first section having a first radius and a second section having a second radius.

In embodiments, the at least one strut comprises at least six struts operatively associated with the at least one cord.

In embodiments, the at least one cord comprises at least two cords and the at least one strut comprises at least two struts.

In embodiments, the at least one cord comprises at least six cords and the at least one strut comprises at least six struts.

In embodiments, the at least one balloon includes an inflation channel in fluid communication with an interior portion of the at least one balloon, wherein the channel is configured to inflate the at least a portion of the at least one balloon by introduction of a fluid through the inflation channel.

In embodiments, the assembly includes a catheter comprising a curved wall extending proximally from the at least one balloon and the inflation channel comprises a curved wall surrounding at least a portion of the catheter.

In embodiments, the at least one balloon comprises a material from the group consisting of: rubber, silicon rubber, latex rubber, polyethylene, polyethylene terephthalate, and polyvinyl chloride.

In embodiments, the filter includes a distal portion, a proximal portion, an opening to the filter associated with the proximal portion, and at least one cord guide channel circumferentially encircling at least a portion the proximal portion. In embodiments, the assembly includes at least one cord, at least a portion of the at least one cord passes through the guide channel, such that at least a portion of the opening is configured to contract radially inwardly in response to tension applied to the at least one cord.

In embodiments, the filter comprises a flexible sheet material and the guide channel is formed from at least one of a bending of a portion of the sheet material, and a shaped component attached to the sheet material.

In embodiments, the at least one cord channel comprises at least two cord channels located substantially on the same cross sectional plane of the filter and the at least one cord comprises at least two cords.

An assembly for filtering debris flowing in an in vivo fluid stream, the assembly comprising at least one balloon configured to volumetrically expand and, during at least a portion of the expansion, operatively connect with a filter, and to contract following the expansion, and a filter comprising a material having tissue connective properties for a tissue associated with an in vivo fluid stream, the filter positioned to operatively connect with the at least one balloon and removably connect to least a portion of the tissue and remain so connected during the contractions of the at least one balloon.

In embodiments, the at least one balloon comprises at least one proximal portion and at least one distal portion. In embodiments, and the operative connection between the at least one balloon and the filter occurs in the at least one proximal portion.

In embodiments, the operative connection between the at least one balloon and the filter occurs in the distal portion.

In embodiments, a maximal expansion diameter of the at least one distal portion is greater than a maximal expansion diameter of the at least one proximal portion.

In embodiments, a maximal expansion diameter of the at least one proximal portion is greater than a maximal expansion diameter of the at least one distal portion.

In embodiments, the at least one balloon comprises at least one angioplasty balloon. In embodiments, the at least one balloon comprises at least two balloons, at least one first balloon and at least one second balloon.

In embodiments, the at least one first balloon is positioned distally to the at least one second balloon. In embodiments, the at least one first balloon has a first maximal inflation diameter that a maximal inflation diameter of the second balloon.

In embodiments, at least a portion of the filter is configured to removably connect to a luminal aspect associated with the fluid stream, in response to pressure by the at least one balloon of between at least about one atmosphere and no more than about 20 atmospheres.

In embodiments, the at least one balloon is configured to sequentially pass through at least two sequences of the expansion and contraction of the at least one balloon. In embodiments, at least a portion of the filter is configured to remain removably connected to a luminal aspect associated with the fluid stream during at least a portion of the at least two sequences.

In embodiments, the assembly includes at least one cord operatively associated with the filter and configured to disconnect at least a portion of the filter from a luminal aspect associated with the fluid stream when tension is applied to the at least one cord.

In embodiments, at least a portion of the filter is configured to disconnect from a luminal aspect associated with the fluid stream when the applied tension to the at least one cord is between at least about one Newton and no more than about 20 Newtons.

In embodiments, at least a portion of the filter includes a pressure-sensitive adhesive having an affinity for a tissue associated with an in vivo luminal aspect. In embodiments, the adhesive is an adhesive from the group of adhesives comprising fibrin, biological glue, collagen, hydrogel, hydrocolloid, collagen alginate, and methylcellulose.

In embodiments, at least a portion of the filter is configured to removably connect to a luminal aspect associated with the fluid stream, in response to pressure by the at least one balloon of between at least about one atmosphere and no more than about 20 atmospheres.

In embodiments, the at least one balloon is configured to contract following the expansion and at least a portion of the filter is configured to remain removably connected to the luminal aspect during the at least one balloon contraction.

In embodiments, the at least one balloon is configured to sequentially pass through at least two sequences of the expansion and contraction of the at least one balloon.

In embodiments, at least a portion of the filter is configured to remain removably connected to the luminal aspect during at least a portion the at least two sequences.

In embodiments, the assembly includes at least one cord operatively associated with the filter and configured to disconnect at least a portion of the filter from the luminal aspect when tension is applied to the at least one cord. In embodiments, at least a portion of the filter is configured to disconnect from the luminal aspect in response to tension applied to the at least one cord of between at least about one Newton and no more than about 20 Newtons.

There is thus provided a method for collecting debris from a stenotic lesion associated with a primary stenotic vessel while preventing passage of the debris into a branch vessel branching from the primary vessel, the method comprising detecting the stenotic lesion in the primary stenotic vessel, locating a filter in the primary stenotic vessel such that an opening of the filter is distal to a center of the stenotic lesion, locating at least a proximal portion an angioplasty balloon proximal to the opening in the filter, expanding the angioplasty balloon, contacting the opening of the filter with at least a distal portion of the angioplasty balloon during the expanding, causing the filter to open during the contacting, generating debris from the stenotic lesion by the expanding of the angioplasty balloon, capturing the debris in the filter, preventing passage of the debris into the branch vessel by the contacting of the opening of the filter with the at least a distal portion of the angioplasty balloon, contracting disengaging the angioplasty balloon, and removing the angioplasty balloon from the primary stenotic vessel.

In embodiments, the method further comprises contracting the filter. In embodiments, the method further comprises removing the filter from the primary stenotic vessel.

There is thus provided a method for collecting debris within a blood vessel, the method comprising juxtaposing an opening of an in vivo debris filter with at least one balloon, expanding the at least one balloon in a blood vessel, opening the filter during the expansion of the at least one balloon, collecting debris within the filter, disengaging the at least one balloon from the filter, and removing the at least one balloon from the vessel.

In embodiments, the method further comprises contracting the filter, and removing the filter from the blood vessel. In embodiments, the method further comprises contacting a stenotic vascular lesion during the expanding.

In embodiments, the method further comprises compressing the lesion during the expanding. In embodiments the method further comprises releasing debris from the lesion during the compressing.

BRIEF DESCRIPTION OF THE DRAWINGS

The invention for safely collecting debris using a debris filter positioned in assembly with an angioplasty balloon is described by way of example with reference to the accompanying drawings. With specific reference now to the drawings in detail, it is stressed that the particulars shown are by way of example and for purposes of illustrative discussion of the preferred method of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the methods of the invention may be embodied in practice.

DESCRIPTION OF THE PREFERRED EMBODIMENTS

Figure 1A:
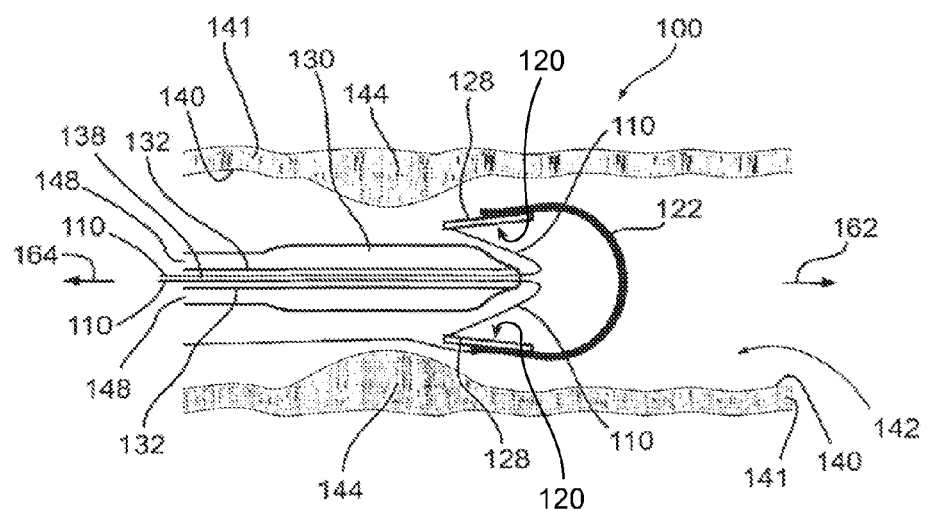
FIG. 1a-1d show deployment of an in vivo filter and balloon assembly in a vessel shown in cross section, according to an embodiment of the invention.

The present invention relates to an in vivo filter that is biased to an open position in conjunction with inflation of an angioplasty balloon. In an exemplary embodiment, during balloon inflation against a stenotic lesion, the balloon presses the outer surface of the filter into a luminal aspect directly upstream from the lesion to capture stenotic debris. The filter maintains thus positioned throughout multiple angioplasty inflations and deflations, following which cords are used to remove the filter from the lumen.

The principles and uses of the teachings of the present invention may be better understood with reference to the accompanying description, Figures and examples. In the Figures, like reference numerals refer to like parts throughout.

Before explaining at least one embodiment of the invention in detail, it is to be understood that the invention is not limited in its application to the details set forth herein. The invention can be implemented with other embodiments, and can be practiced or carried out in various ways.

It is also understood that the phraseology and terminology employed herein is for descriptive purpose and should not be regarded as limiting.

Unless otherwise defined, all technical and scientific terms used herein have the same meaning as commonly understood by one of ordinary skill in the art to which the invention belongs. In addition, the descriptions, materials, methods, and examples are illustrative only and not intended to be limiting. Methods and materials similar or equivalent to those described herein can be used in the practice or testing of the present invention.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

As used herein, "a" or "an" mean "at least one" or "one or more". The use of the phrase "one or more" herein does not alter this intended meaning of "a" or "an".

Filter Assembly 100

FIG. 1a shows an exemplary representation of an in vivo debris filter assembly 100 of the present invention, in a cross section of a blood vessel 141. A filter 122 is shown in a contracted, pre-dilated, position with loose cords 110 attached to two struts 128 that are connected to filter 122. Cords 110 exit filter 122 and pass through a lumen 138 and into and through a catheter 132. Cords 110 typically exit lumen 138 ex vivo, thereby allowing ex vivo manipulation by an operator.

A balloon 130 projects downstream of catheter 132 and is positioned adjacent a stenotic lesion 144. Balloon 130 typically comprises a biologically compatible elastomeric material, or semi compliance material, for example: rubber, silicon rubber, latex rubber, polyethylene, polyethylene terephthalate, Mylar, and/or polyvinyl chloride.

Figure 1B:
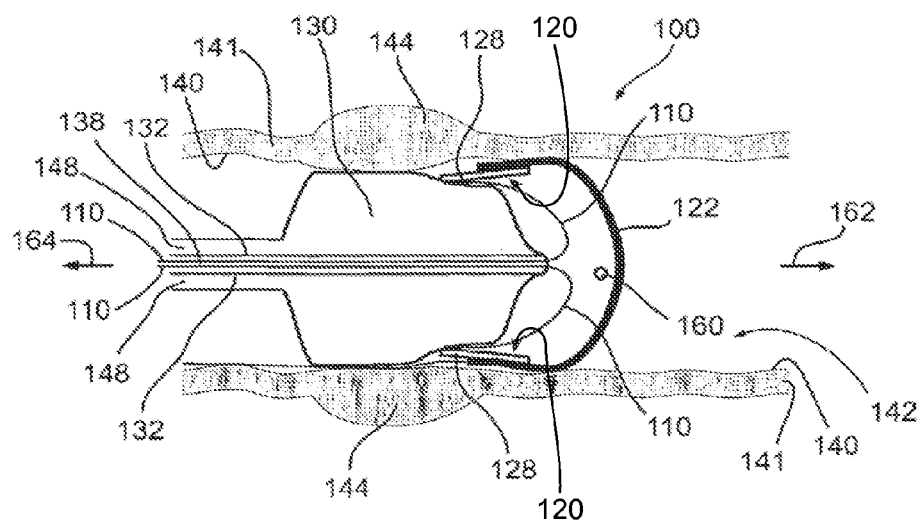

In FIG. 1b, balloon 130 has been inflated by introducing fluid through a fluid channel 148 that is substantially coaxial to catheter 130. During inflation of balloon 130, after the diameter of balloon 130 reaches the distance between struts 128, continued inflation of balloon 130 causes struts 128 to bias radially outwardly, thereby expanding filter 122.

Once inflated, filter 122 filters debris 160 that is released from stenotic lesion 144 and continues to filter debris 160 even as balloon 130 is deflated, as explained below.

While filter 122 is shown in an expanded position as a generally curved structure, balloon 130 may alternatively have a variety of shapes, including a conus having an apex located downstream of balloon 130.

Filter 122 typically comprises a mesh sheet material that is configured to filter debris 160 from a lumen 142. Filter 122 typically includes apertures having diameters of between at least about 20 microns and no more than about 200 microns in diameter.

Additionally, filter 122 and/or struts 128, are configured to flex outward until such flexion is limited by a luminal aspect 140, for example a diameter of between 3.0 and 6.0 millimeters, depending on the size of lumen 142 in which filter 122 is deployed.

In further embodiments, portions of filter 122 and/or struts 128 comprise super elastic material, for example nitinol; an elastic material; and/or a plastic material; the many materials and their properties being well-known to those familiar with the art.

Similarly balloon 130 has an inflation diameter of between 3.0 and 6.0 millimeters, depending on the cross sectional diameter of lumen 142. In larger vessels 141, balloon 130 and filter 122 optionally are manufactured to have larger maximal diameters. In smaller vessels, for example to cut down on the bulk of deflated balloon 130 and filter 122, smaller maximal diameters are optionally appropriate.

Filter 122 comprises materials and/or apertures that aid in removably connecting filter 122 to an in vivo luminal aspect 140. In this manner, filter 122 remains connected to luminal aspect 140 for a period of time after balloon 130 has deflated, herein contracted, by egress of fluid through channel 148. By remaining in contact with luminal aspect 140, filter 122 continues to filter debris 160 that may be released into lumen 142 from lesion 144 while balloon 130 is in a contracted state.

In some embodiments, the material and configuration of filter 122 ensures that filter 122 remains removably connected to luminal aspect 140 following deflation of balloon 130. In other embodiments, filter 122 includes a pressure sensitive adhesive having an affinity for luminal aspect 140 so that the adhesive, optionally in conjunction with the material of filter 130, remain removably connect to vessel luminal aspect 140 following deflation of balloon 130.

There are many adhesives that may be contemplated for use in providing a removable connection of filter 122 to luminal aspect 140 including, inter alia: fibrin, biological glue, collagen, hydrogel, hydrocolloid, collagen alginate, and methylcellulose, to name a few.

Whether filter 122 comprises a mesh material alone or in combination with an adhesive, filter 122 is optionally configured to removably connect to luminal aspect 140 from a pressure exerted by balloon 130 of, for example, between one and twenty atmospheres.

In further exemplary embodiments, for example when there is continued danger of debris 160 being generated after lesion 144 has been compressed, balloon 130 is optionally deflated and removed from lumen 142 while filter 122 is left in place. Filter 122 optionally is left connected to luminal aspect 140 by the configuration of filter 122 and/or biological glues noted above until the danger of generation of debris 160 has passed.

As noted above, during a typical balloon angioplasty, balloon 130 is sequentially inflated to a pressure of several atmospheres and deflated. In exemplary embodiments, filter 122 remains removably connected to luminal aspect 140 following the first inflation of balloon 130 and throughout several sequences of inflation and deflation.

As filter 122 is deployed relatively proximate to lesion 144 where luminal aspect 140 generally comprises unhealthy tissue, the chance that filter 122 will cause damage to healthy tissue of luminal aspect 140 is very low.

Additionally, the proximity of filter 122 to balloon 130 substantially lowers the odds that a branch artery will be located between filter 122 and balloon 130, to act as a conduit for debris 160. Further, as balloon 130 and filter 122 are deployed on single catheter 132, the cost for each assembly 100 should be lower than existing technology employing a separate filter. Moreover, as assembly 100 includes balloon 130 and filter 122 mounted on a single catheter, the complexity of manufacture, deployment and the surgical fees to the surgeon should be reduced over existing technology.

Figure 1C:
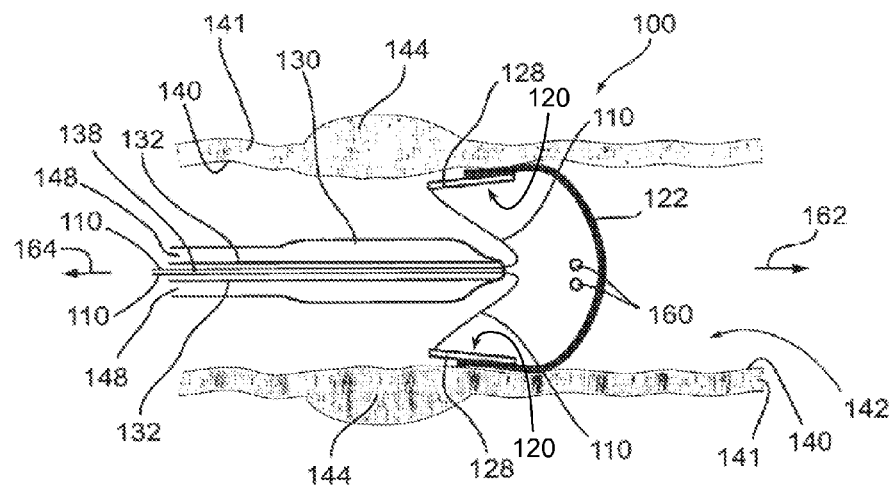
Figure 1D:
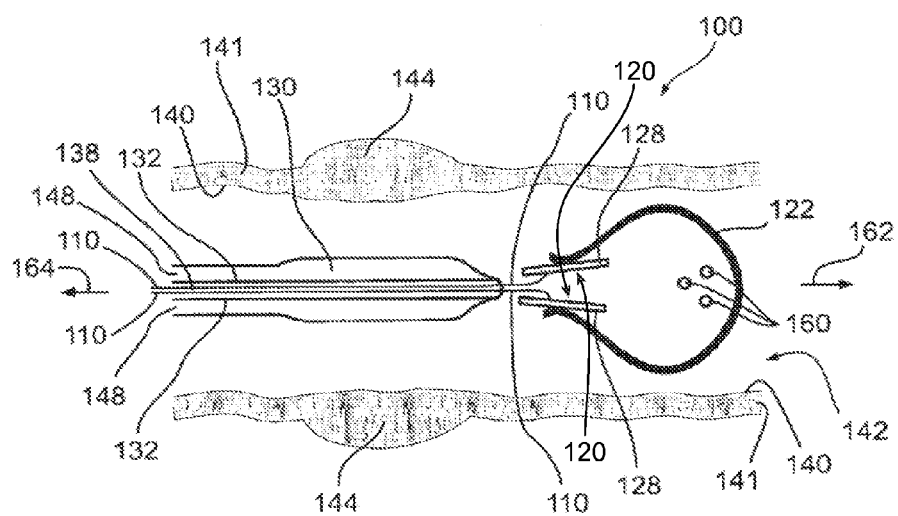

As seen in FIG. 1c, after stenotic lesion 144 has been cracked and squashed radially outwards, balloon 130 is deflated and filter 122 remains in an expanded state and continues to capture debris 160. As the fluid contained in lumen 142 is moving in a direction 162, in a distal or downstream direction with respect to filter 122, debris 160 remains in place, captured within filter 122.

As used herein, the terms distal and distally refer to a position and a movement, respectively, in downstream direction 162.

To disconnect filter 122 from luminal aspect 140, cords 110 are pulled proximally, upstream, in a direction 164. As used herein, the terms proximal and proximally refer to a position and a movement, respectively, in upstream direction 164.

While cords 110, as shown, pass through catheter lumen 138, in alternative embodiments, cords 110 pass to the side of balloon 130 without passing through a lumen 138. Further, while balloon 130 is shown attached to catheter, 132, there are many alternative options for delivering balloon 130 and filter 122, for example using a guide wire. Those familiar with the art will readily recognize the many alternative modes and configurations available for delivery and operation of balloon 130 and filter 122.

In an exemplary embodiment, filter 122 is configured to disconnect from luminal aspect 140 in response to tension applied to cords 110 of at least about one Newton and no more than about 20 Newtons.

As the diameter of lumen 142 is larger than the diameter of catheter lumen 138, continued upstream pull in direction 164 on cords 110, biases the proximal portions of struts 128 radially inward, causing the proximal edges of filter 122 to move radially inward so that filter 122 disconnects from luminal aspect 140. Following disconnection of filter 122 from luminal aspect 140, continued pulling of cords 110 in direction 164 causes struts 128 to inwardly bias, thereby reducing the upstream cross sectional diameter of filter 122.

As the fluid in lumen 142 travels distally in direction 162, pulling catheter 132 and filter 122 in proximal direction 164 causes debris 160 to move downstream against filter 122 so that debris 160 remains captured by filter 122.

Thus, filter 122 maintains captured debris 160 even when there is a distance between struts 128, as might occur when there is considerable volume of debris 160, for example in large arteries. Optionally, cords 110 are pulled in direction 164 until a portion of filter 122 contacts balloon 130 and/or enters catheter lumen 138.

While two struts 128 are shown connected to two cords 110, the present embodiments, contemplate four or even eight struts 128, with each strut 128, or each pair of struts 128, being attached to individual cords 110 that remove filter 122 from luminal aspect 140.

Alternatively, assembly 100 contemplates using a single strut 128 with a single cord 110 connected to single strut 128 that encircles filter 122 and slidingly attaches to strut 128 in a lasso configuration. Pulling on single cord 110 causes contraction of struts 128 and of the associated cross-sectional circumference of filter 122, thereby preventing egress of debris 160 filter 122. The many options available for configuring cords 110 and struts 128 to effectively close filter 122 are well known to those familiar with the art.

Filter Assembly 200

Figure 2A:
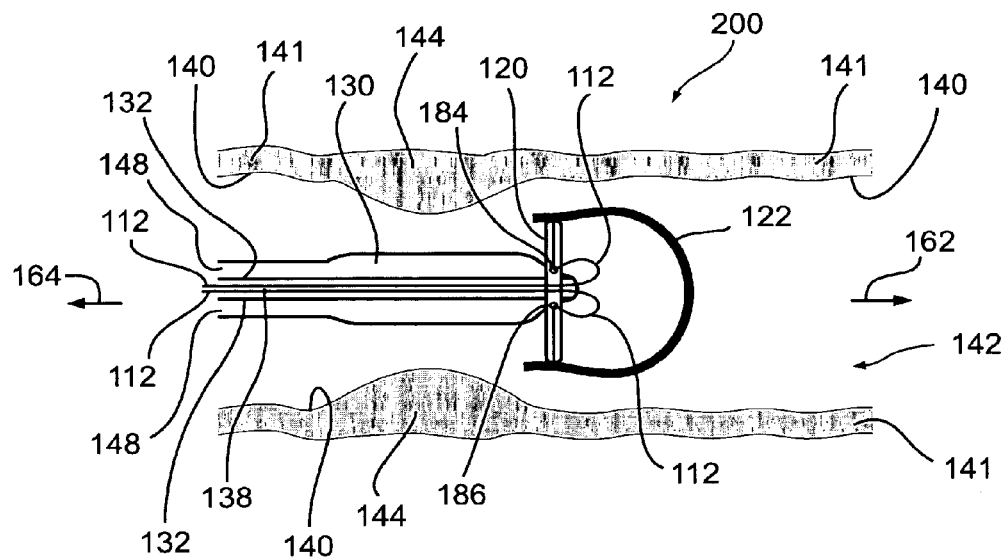
FIGS. 2a-2d, 3a-3c, 4, and 5a-5e show alternative embodiments of the filter and balloon assembly shown in FIGS. 1a-1d, according to the invention.
Figure 2B:
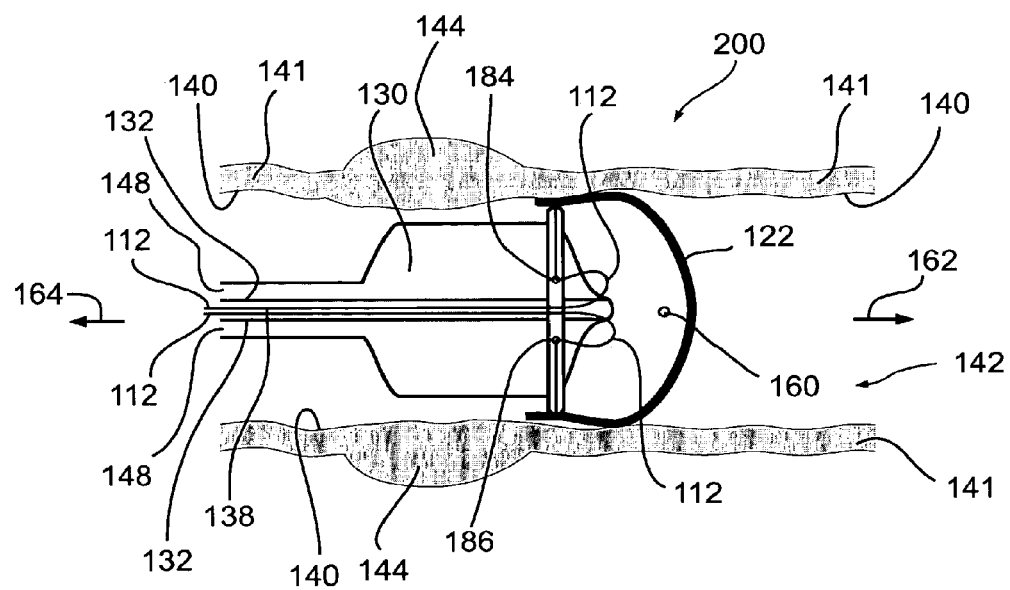
Figure 2C:
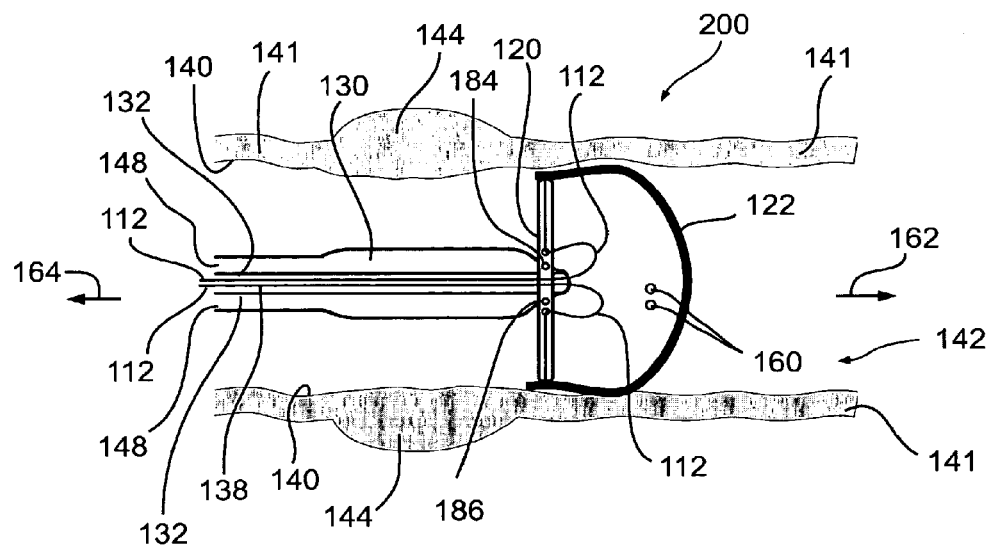

FIG. 2a shows an exemplary embodiment of an assembly 200 in which a single cord 112 passes distally in direction 162 through catheter lumen 138. Cord 112 then curves within filter 122 to pass in a proximal direction 164 into a cord inlet 184 and through a cord channel 120. Cord channel 120 guides cord 112 circumferentially around filter 122. After circling filter 122, cord 112 exits channel 120 through cord outlet 186 and passes distally in direction 162 into filter 122. Cord 112 then curves within filter 122 to pass in a proximal direction 164 into and through catheter lumen 138.

Figure 2D:
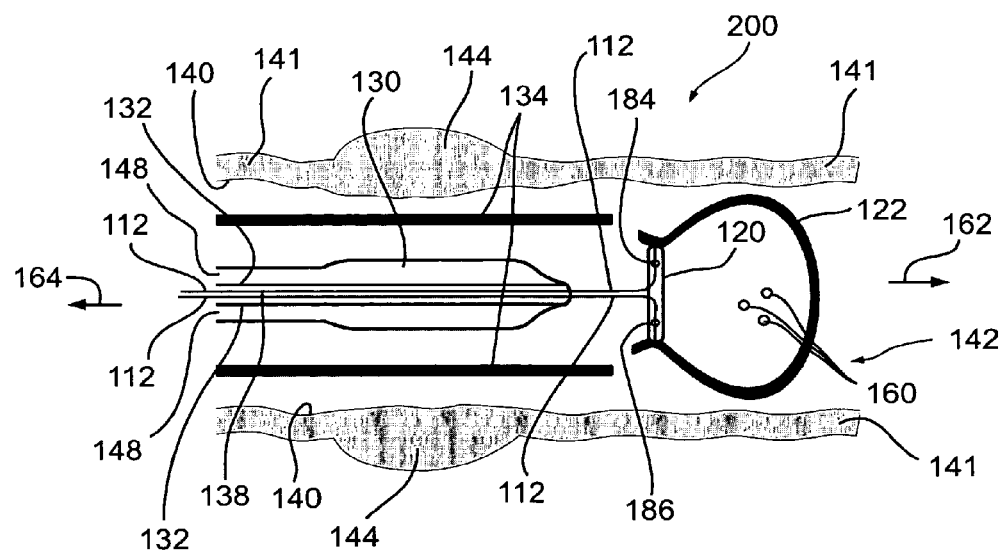

In this manner both ends of cord 112 exit catheter lumen 138 and, by pulling both ex vivo ends of cord 112 in direction 164, filter 122 is contracted along channel 120, as seen in FIG. 2d. While a single cord 112 is shown, channel 120 optionally comprises multiple pairs of inlets 184 and outlets 186, each associated with a separate cord 112. The many configurations and modifications of channel 120, inlet 184, and outlet 186 are well known to those familiar with the art.

FIG. 2d shows an exemplary embodiment of a tubular compression sleeve 134 that is coaxial with catheter 132. Sleeve 134 has been slidingly pushed through vessel lumen 142 in direction 162 until sleeve 134 approaches filter 122.

In an exemplary embodiment, pulling cord 112 and/or catheter 132 in direction 164 while holding sleeve 134 substantially stationary pulls filter 122 into compression sleeve 134. Alternatively, compression sleeve 134 is advanced in direction 162 while catheter 132 and/or cord 110 are held substantially stationary.

In an exemplary embodiment, compression sleeve 134 serves as a housing for filter 122 to prevent filter 122 from scraping along luminal aspect 140 during removal from lumen 142. Additionally or alternatively, compression sleeve 134 serves to compress filter 122 into a smaller maximal circumferential diameter so that filter 122 more easily passes through lumen 142 during removal of filter 122.

Balloon Assembly 300

Figure 3A:
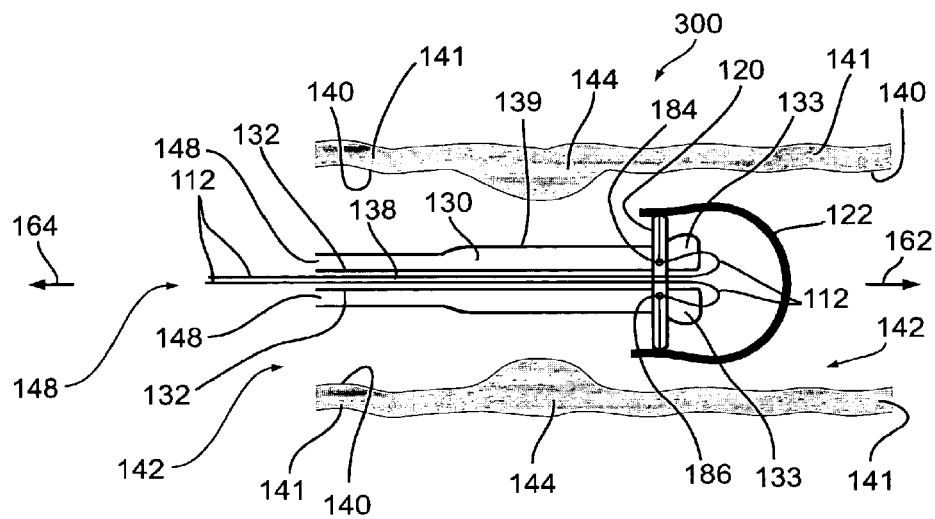

In embodiments, balloon 130 optionally includes alternative shapes, for example having varied cross sectional diameters. As seen in assembly 300 (FIG. 3a), the diameter associated with a distal portion 133 of deflated balloon 130 is larger than the diameter associated with a proximal portion 139.

Figure 3B:
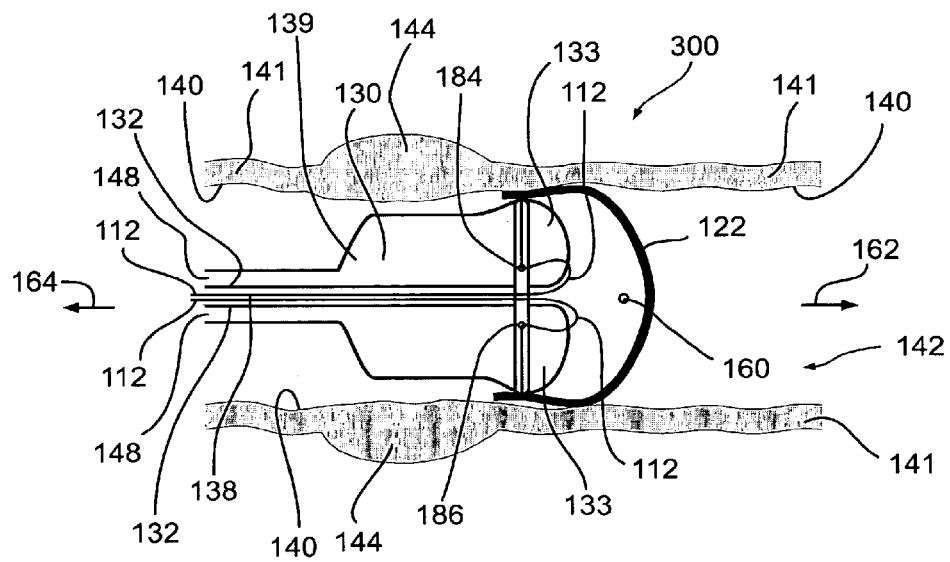

As seen in FIG. 3b, filter 122 reaches a maximal diameter initially as distal balloon portion 133 inflates. In this manner, filter 122 is fully in position and expanded prior to inflation of proximal balloon portion 139.

Figure 3C:
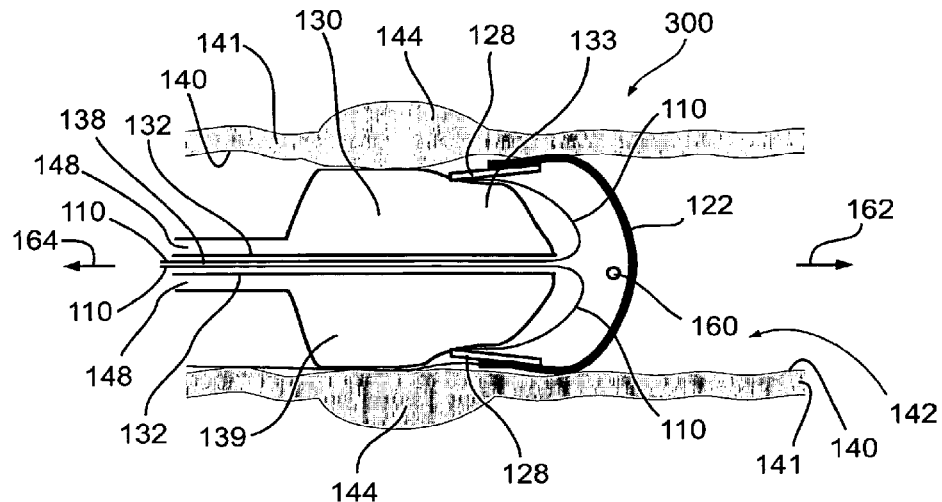

As seen in FIG. 3c, proximal balloon portion 139 has been fully inflated to compress lesion 144, thereby releasing debris 160 that is captured by filter 122. The many options for configuring alternative shapes of balloon 130 are well known to those familiar with the art.

Balloon and Filter Assembly 400

Figure 4:
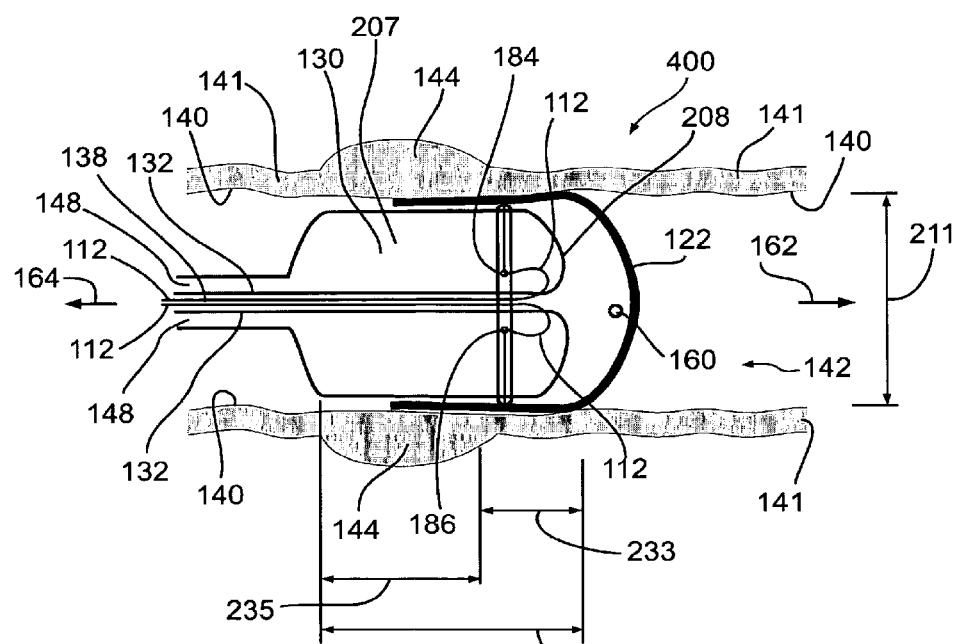

There are additionally many methods of assembling filter 122 and balloon 130, as seen in assembly 400 (FIG. 4). In a non-limiting embodiment, balloon 130 is seen having an overall length 209 of approximately 38 millimeters and a maximal inflation diameter 211 of approximately 5 millimeters.

Additionally, balloon 130 is shown with a proximal portion 207 having a length 235 of approximately 18 millimeters and a distal portion 208 having a length 233 of approximately 18 millimeters.

In an exemplary embodiment, filter 122 extends to substantially cover distal portion 208 while proximal portion 207 is unprotected by filter 122.

In alternative configurations of assembly 400, filter 122 optionally substantially fully covers distal balloon portion 208 and extends over at least a portion of proximal balloon portion 207; the many configurations of assembly 400 being well known to those familiar with the art.

Dual Balloon Assembly 500

Figure 5A:
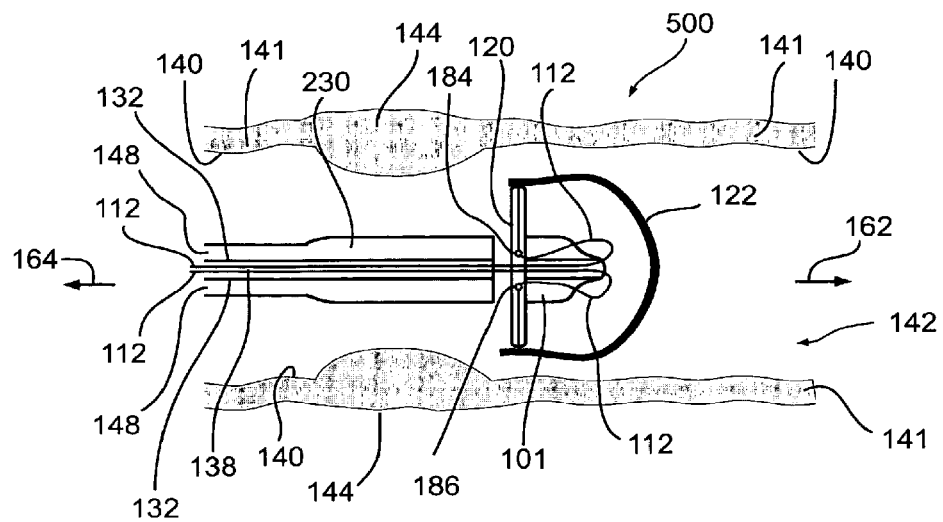
Figure 5B:
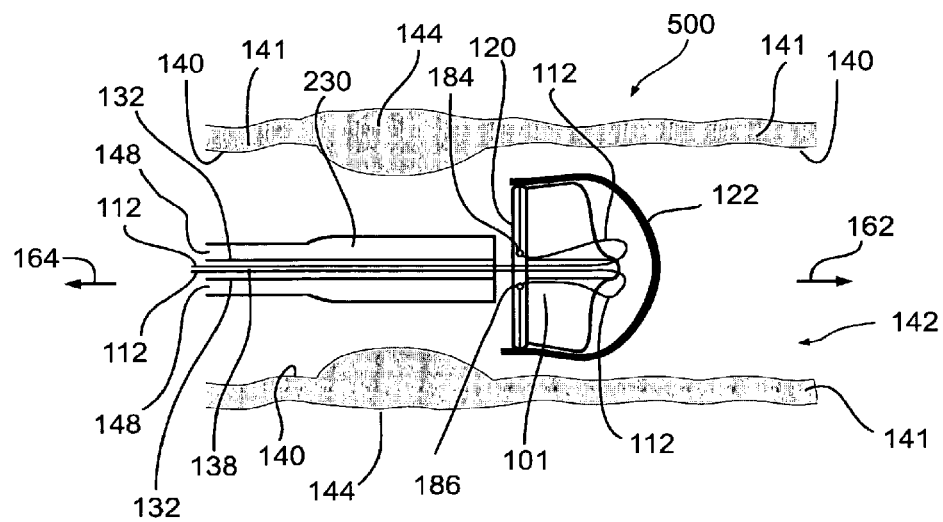
Figure 5C:
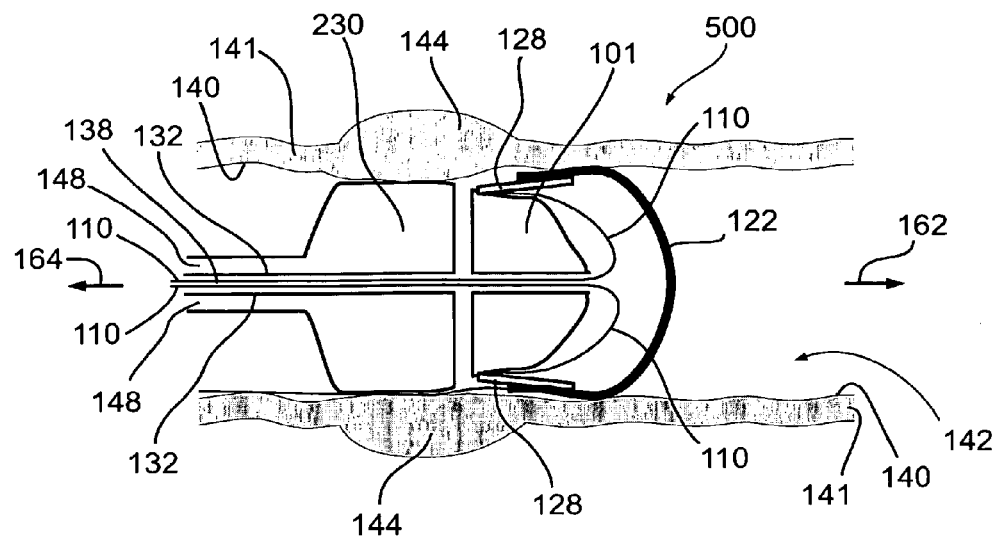

Assembly 500 (FIGS. 5a-5e) demonstrates just one more of the many embodiments of the instant invention that are easily contemplated by those familiar with the art. Assembly 500 comprises a proximal balloon 230 and a distal balloon 101. As seen in FIG. 5b, distal balloon 101 is inflated to expand filter 122 and substantially take up the volume within filter 122. As seen in FIG. 5c, proximal balloon 230 is inflated separately and pressed against lesion 144.

Figure 5D:
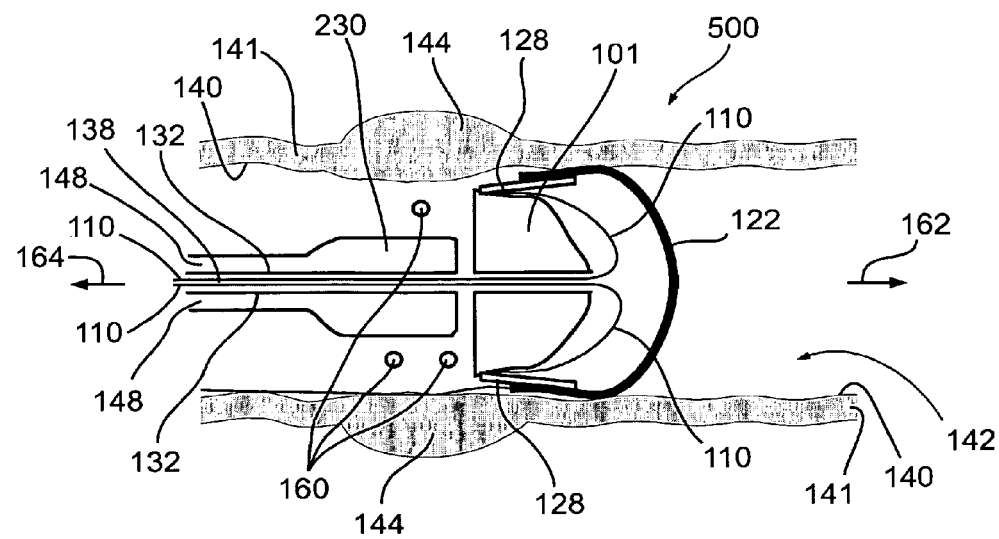
Figure 5E:
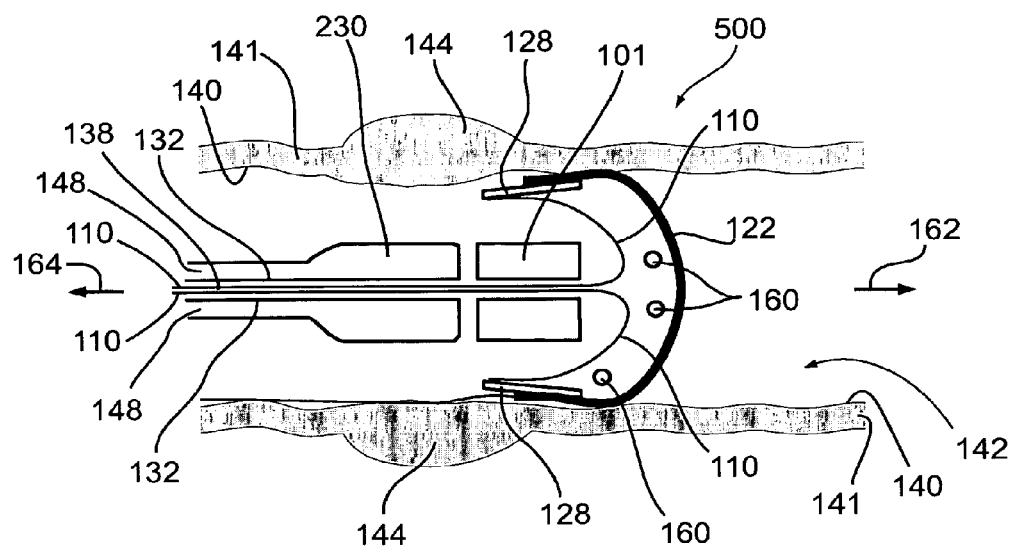

After deflation of proximal balloon 230 as seen in FIG. 5d, distal balloon 101 remains inflated so that debris 160 remains proximal to distal balloon 101. Upon deflation of distal balloon 101, debris 160 enters and is captured by filter 122.

Alternative Environments

While assemblies 100-500 have been described with respect to vessel 141, assemblies 100-500 can be easily configured for use in a wide variety of in vivo lumens 142 including inter alia: a lumen of a urethra, a biliary lumen and/or a renal calyx lumen. Additionally or alternatively, filter 122 can be easily modified to capture debris in virtually any in vivo lumen 142 including, inter alia: biliary stones and/or renal stones. The many applications, modifications and configurations of assemblies 100-500 for use in virtually any in vivo lumen 142 will be readily apparent to those familiar with the art.

Materials and Design

In embodiments, filter 122 comprises a sheet material configured to extend distally with respect to balloon 130 while filter 122 is expanded. In embodiments, the sheet material of filter 122 is selected from the group consisting of: meshes and nets.

In embodiments, bending of a portion of the sheet material of filter 122 forms filter cord channel 120. In embodiments, attaching a shaped component to filter 122 forms filter cord channel 120.

In embodiments, the material of filter 122 has a thickness of at least about 20 microns. In embodiments, the material of filter 122 has a thickness of no more than about 200 microns. In embodiments, the material of filter 122 includes apertures having diameters of at least about 20 microns. In embodiments, the material of filter 122 includes apertures having diameters of no more than about 80 microns in diameter. In embodiments, the material of filter 122 is manufactured using a technique from the group of techniques consisting of: interlacing, knitting, weaving, braiding, knotting, wrapping, and electro spinning.

In embodiments, filter 122 is configured to expand to a cross sectional diameter of at least about 1.0 millimeters. In embodiments, filter 122 is configured to expand to a cross sectional diameter of no more than about 6.0 millimeters. In embodiments, the extent of the expansion of filter 122 is configured to be limited by the walls of luminal aspect 140 in which filter 122 is deployed.

In embodiments, balloon 130 has a maximum inflation diameter of at least about 1.0 millimeter. In embodiments, balloon 130 has a maximum inflation diameter of no more than about 6.0 millimeters.

In embodiments, balloon 130 has a wall thickness of at least about 0.2 millimeters. In embodiments, balloon 130 has a wall thickness of no more than about 0.5 millimeters.

In embodiments, strut 128 has a substantially circular cross section having a diameter of at least about 0.1 millimeters. In embodiments, strut 128 has a substantially circular cross section having a diameter of no more than about 0.6 millimeters.

In embodiments, strut 128 has a cross section having greater and lesser measurements and the greater measurement is at least about 0.1 millimeters. In embodiments, strut 128 has a cross section having greater and lesser measurements and the greater measurement is no more than about 0.6 millimeters. In embodiments, strut 128 has a cross section having greater and lesser measurements and the lesser measurement is at least about 0.1 millimeters. In embodiments, strut 128 has a cross section having greater and lesser measurements and the lesser measurement is no more than about 0.6 millimeters.

In embodiments, filter 122 has an internal and an external aspect and strut 128 is attached to the internal aspect or the external aspect of filter 122. In embodiments, strut 128 is attached to filter 122 using a process selected from the group consisting of: sewing, adhesion, gluing, suturing, riveting and welding.

In embodiments, cord channel 120 comprises at least two cord channels; and cord 112 comprises at least two cords.

In embodiments, catheter 132 has an outside diameter of at least about 1.0 millimeter. In embodiments, catheter 132 has an outside diameter of no more than about 5.0 millimeters. In embodiments, catheter 132 has a length of at least about 0.8 meter. In embodiments, catheter 132 has a length of no more than about 1.5 meters.

In embodiments, the walls of catheter 132 compression sleeve 134 have a thickness of at least about 2 millimeters. In embodiments, the walls of catheter 132 compression sleeve 134 have a thickness of more than about 5 millimeters.

In embodiments, filter 122, cord 110 (FIG. 1*a*) and cord 112 (FIG. 2*a*), strut 128, compression sleeve 134, and catheter 132, comprise a material from the group consisting of: polyethylene, polyvinyl chloride, polyurethane and nylon.

In embodiments, filter 122, cord 110 (FIG. 1*a*) and cord 112 (FIG. 2*a*), strut 128, compression sleeve 134, and catheter 132, comprise a material selected from the group consisting of: nitinol, stainless steel shape memory materials, metals, synthetic biostable polymer, a natural polymer, and an inorganic material. In embodiments, the biostable polymer comprises a material from the group consisting of: a polyolefin, a polyurethane, a fluorinated polyolefin, a chlorinated polyolefin, a polyamide, an acrylate polymer, an acrylamide polymer, a vinyl polymer, a polyacetal, a polycarbonate, a polyether, an aromatic polyester, a polyether (ether keto), a polysulfone, a silicone rubber, a thermoset, and a polyester (ester imide).

In embodiments the natural polymer comprises a material from the group consisting of: a polyolefin, a polyurethane, a Mylar, a silicone, a polyester and a fluorinated polyolefin.

In embodiments, filter 122, cord 110 (FIG. 1*a*) and cord 112 (FIG. 2*a*), strut 128, compression sleeve 134, and catheter 132, comprise a material having a property selected from the group consisting of: compliant, flexible, plastic, and rigid.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art.

Accordingly, the invention is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An assembly for filtering debris flowing in an in vivo fluid stream, the assembly comprising:
   i) at least one balloon configured to volumetrically expand and, during at least a portion of said expansion, operatively connect with a filter, and to contract following said expansion;
   ii) a filter configured to operatively connect with said at least one balloon during at least a portion of said volumetric expansion of said at least one balloon, such that said filter expands during said operative connection in order to filter debris from a fluid flowing in a fluid stream within which said expanded filter is disposed, wherein said filter includes:
   a) a distal portion;
   b) a proximal portion;
   c) an opening to said filter associated with said proximal portion; and
   d) wherein at least one cord guide channel circumferentially encircling at least a portion said proximal portion and comprises two cord channels located substantially on the same cross-sectional plane of the filter, and wherein at least two cords are disposed in each of the cord channels to connect to the filter.

2. The assembly according to claim 1, wherein at least a portion of said filter is configured to removably connect to a luminal aspect associated with said fluid stream, in response to pressure of between at least about one atmosphere and no more than about 20 atmospheres.

3. The assembly according to claim 1, wherein at least a portion of said filter is configured to remain removably connected to a luminal aspect during said contraction of said at least one balloon.

4. The assembly according to claim 3, including at least one cord passing through said at least one cord guide channel and operatively associated with said filter and configured to disconnect at least a portion of said filter from said luminal aspect when tension is applied to said at least one cord.

5. The assembly according to claim 4, wherein said at least a portion of said filter is configured to disconnect from said luminal aspect in response to tension applied to said at least one cord of at least about one Newton.

6. The assembly according to claim 4 wherein said at least a portion of said filter is configured to disconnect from said luminal aspect in response to tension applied to said at least one cord of no more than about 20 Newtons.

7. The assembly according to claim 4, wherein: i) said at least one balloon comprises an outer wall having a distal end and a proximal end and an inner wall defining a lumen, said lumen extending from said distal end to said proximal end; and ii) at least a portion of said at least one cord is configured to slidingly pass through said lumen.

8. The assembly according to claim 7, including a catheter having a distal end and a proximal end and a lumen extending from said distal end to said proximal end, wherein said at least one balloon proximal end is operatively associated with said distal end of said catheter.

9. The assembly according to claim 8, wherein said at least one balloon lumen is substantially continuous with said catheter lumen.

10. The assembly according to claim 8, wherein at least a portion of said at least one cord additionally extends through said catheter lumen.

11. The assembly according to claim 3, including a compression sleeve comprising a substantially curved wall having a proximal end, a distal end and a lumen extending from said proximal end to said distal end, said lumen having a cross sectional diameter that is substantially smaller than the maximal cross sectional diameter of said luminal aspect.

12. The assembly according to claim 11, including at least one cord passing through said at least one cord guide channel and operatively associated with said filter, at least a portion of said at least one cord movingly juxtaposed within said compression sleeve lumen.

13. The assembly according to claim 12 wherein when said at least one cord operatively associated with said filter is held relatively stationary during a first distal moving of said compression sleeve, said filter is caused to disconnect from said luminal aspect.

14. The assembly according to claim 12, wherein in response to at least one second distal moving of said sleeve while said at least one cord is held relatively stationary, said filter is caused to radially contract such that a maximal cross sectional diameter of said filter is smaller than a cross sectional diameter of said sleeve lumen.

15. The assembly according to claim 14, wherein in response to at least one third distal moving of said sleeve while said at least one cord is held stationary, at least a portion of said filter is caused to enter said sleeve lumen.

16. The assembly according to claim 1, wherein at least a portion of said filter includes a pressure-sensitive adhesive having an affinity for a tissue associated with an in vivo luminal aspect.

17. The assembly according to claim 1, wherein said filter comprises a flexible sheet material and said guide channel is formed from at least one of: a bending of a portion of said sheet material; and a shaped component attached to said sheet material.

18. The assembly according to claim 1, including at least one cord, at least a portion of said at least one cord passes through said guide channel, such that at least a portion of said opening is configured to contract radially inwardly in response to tension applied to said at least one cord.

19. The assembly according to claim 18, wherein said at least one cord channel comprises at least two cord channels and said at least one cord comprises at least two cords, said at least two cord channels being located substantially on the same cross sectional plane of said filter.

20. An assembly for filtering debris flowing in an in vivo fluid stream, the assembly comprising:
  i) at least one balloon configured to volumetrically expand and to contract following said expansion; and
  ii) a filter comprising a material having tissue connective properties for a portion of luminal tissue associated with an in vivo fluid stream, said filter positioned to operatively connect with said at least one balloon during at least a portion of said expansion and removably connect to least a portion of said tissue and remain so connected during said contraction of said at least one balloon,
wherein said filter includes:
  a) a distal portion;
  b) a proximal portion;
  c) an opening to said filter associated with said proximal portion; and
  d) wherein at least one cord guide channel circumferentially encircling at least a portion said proximal portion and comprises two cord channels located substantially on the same cross-sectional plane of the filter, and wherein at least two cords are disposed in each of the cord channels to connect to the filter.

* * * * *

UNITED STATES PATENT AND TRADEMARK OFFICE
CERTIFICATE OF CORRECTION

PATENT NO. : 9,132,261 B2
APPLICATION NO. : 13/237977
DATED : September 15, 2015
INVENTOR(S) : Holzer et al.

Page 1 of 1

It is certified that error appears in the above-identified patent and that said Letters Patent is hereby corrected as shown below:

In the claims,

Claim 1 at Column 14, line 6: Please change --encircling-- to "encircles".

Claim 1 at Column 14, line 6: Please insert --of-- after "portion".

Claim 20 at Column 16, line 20: Please change --encircling-- to "encircles".

Claim 20 at Column 16, line 20: Please insert --of-- after "portion".

Signed and Sealed this
Ninth Day of February, 2016

Michelle K. Lee
*Director of the United States Patent and Trademark Office*